United States Patent
Sniadecki et al.

(10) Patent No.: US 11,331,027 B2
(45) Date of Patent: May 17, 2022

(54) SYSTEM FOR MAGNETIC DETECTION OF MYOCARDIAL FORCES

(71) Applicant: University of Washington, Seattle, WA (US)

(72) Inventors: Nathan J. Sniadecki, Bothell, WA (US); Shiv Bhandari, Seattle, WA (US); Kevin S. Bielawski, Seattle, WA (US); Andrea B. Leonard, Seattle, WA (US); Charles E. Murry, Seattle, WA (US)

(73) Assignee: University of Washington, Seattle, WA (US)

( * ) Notice: Subject to any disclaimer, the term of this patent is extended or adjusted under 35 U.S.C. 154(b) by 924 days.

(21) Appl. No.: 16/082,847

(22) PCT Filed: Mar. 10, 2017

(86) PCT No.: PCT/US2017/021899
§ 371 (c)(1),
(2) Date: Sep. 6, 2018

(87) PCT Pub. No.: WO2017/156455
PCT Pub. Date: Sep. 14, 2017

(65) Prior Publication Data
US 2019/0029549 A1    Jan. 31, 2019

Related U.S. Application Data

(60) Provisional application No. 62/307,157, filed on Mar. 11, 2016.

(51) Int. Cl.
*A61B 5/243*    (2021.01)
*A61B 5/00*    (2006.01)
(Continued)

(52) U.S. Cl.
CPC ............ *A61B 5/243* (2021.01); *A61B 5/7203* (2013.01); *A61B 5/7225* (2013.01); *C12M 21/08* (2013.01);
(Continued)

(58) Field of Classification Search
None
See application file for complete search history.

(56) References Cited

U.S. PATENT DOCUMENTS 6,424,853 B1    7/2002    Tsukada et al.
8,586,368 B2    11/2013    Superfine et al.
(Continued)

FOREIGN PATENT DOCUMENTS

EP    1783206    5/2007
WO    2013169379    11/2013
WO    WO-2013169379 A1 *  11/2013    ......... G01N 33/4905

OTHER PUBLICATIONS

Author unknown; International Search Report and Written Opinion of PCT/US2017/21899; dated Jun. 1, 2017; 9 pgs.
(Continued)

*Primary Examiner* — Teresa E Knight
(74) *Attorney, Agent, or Firm* — Christensen O'Connor Johnson Kindness PLLC

(57) ABSTRACT

Devices and techniques for magnetic detection of myocardial forces are generally described. In some examples, cardiac tissue may be cultured such that the cardiac tissue adheres to a first post and a second post. In further examples, a magnetometer may detect a change in a magnetic field resulting from a deflection of the first post in a first direction from a first position to a second position. In some other examples a signal corresponding to the change in the magnetic field may be generated. In still other examples, frequencies of the signal outside of a first frequency range may
(Continued)

be excluded to produce a filtered signal. In various examples, the first frequency range may include frequencies associated with beating of cardiac tissue. In still further examples, a force exerted by the cardiac tissue may be determined based at least in part on the filtered signal.

22 Claims, 7 Drawing Sheets

(51) Int. Cl.
  C12M 1/42         (2006.01)
  C12M 3/00         (2006.01)
  G01N 27/72        (2006.01)
  G01N 33/483       (2006.01)
(52) U.S. Cl.
  CPC ............ *C12M 35/06* (2013.01); *G01N 27/72* (2013.01); *G01N 33/4833* (2013.01); *A61B 2503/02* (2013.01); *A61B 2562/0223* (2013.01)

(56) References Cited

U.S. PATENT DOCUMENTS

| | | |
|---|---|---|
| 9,140,684 B2 | 9/2015 | Sniadecki et al. |
| 9,213,024 B2 | 12/2015 | Sniadecki et al. |
| 9,857,356 B2 | 1/2018 | Parker et al. |
| 9,952,149 B2 | 4/2018 | Superfine et al. |
| 2003/0091979 A1 | 5/2003 | Eschenhagen |
| 2007/0085534 A1 | 4/2007 | Seki et al. |
| 2010/0101308 A1 | 4/2010 | Superfine et al. |
| 2016/0030177 A1 | 2/2016 | Eschenhagen et al. |

OTHER PUBLICATIONS

Snaidecki et al.; Magnetic Microposts for Mechanical Stimulation of Biological Cells: Fabrication, Characterization, and Analysis; Scholarly Commons; University of Pennsylvania; 2008.
Morrish; The Physical Principles of Magnetism; Chapter 1; Jan. 1, 2001; 31 pgs; The Institute of Electrical and Electronics Engineers, Inc.
Hibbeler: Mechanics of Materials, 8th Edition; Chapters 9 & 11; 2001; 124 pgs; Pearson Prentice Hall.
Harris et al.; Silicone Rubber Substrata: A New Wrinkle in the Study of Cell Locomotion; Science, New Series; Apr. 11, 1980; pp. 177-179; vol. 208; No. 4440; JSTOR.
Cheng-Zhang et al.; The Influence of the Packing Density on the Magnetic Behaviour of Alumite Media; Journal of Magnetism and Magnetic Materials; 1990; pp. 236-246; vol. 88.
Mulieri et al.; ; Altered Myocardial Force-Frequency Relation in Human Heart Failure; Circulation; Jan. 7, 1992 pp. 1743-1750; vol. 85.
Wang et al.; Mechanotransduction Across the Cell Surface and Through the Cytoskeleton; Science; May 21, 1993; pp. 1124-1127; vol. 260; No. 5111; American Association for the Advancement of Science.
Lee et al.; Traction Forces Generated by Locomoting Keratocytes; The Journal of Cell Biology; Dec. 15, 1994; pp. 1957-1964; vol. 127; No. 6; Department of Cell Biology and Anatomy and Lineberger Comprehensive Cancer Center, University of North Carolina; North Carolina.
Dembo et al.; Imaging the Traction Stresses Exerted by Locomoting Cells with the Elastic Substratum Method; Biophysical Journal; Apr. 1996; pp. 2008-2022; vol. 70
Choquet et al.; Extracellular Matrix Rigidity Causes Strengthening of Integrin-Cytoskeleton Linkages; Cell; Jan. 10, 1997; pp. 39-48; vol. 88.
Eschenhagen et al.; Three-dimensional Reconstitution of Embryonic Cardiomyocytes in a Collagen Matrix: A New Heart Muscle Model System; FASEB Journal; Jul. 1997; pp. 683-694; vol. 11.

Xia et al.; Soft Lithography; Angewandte Chemie Int.; 1998; pp. 550-575; vol. 37; Wiley-VCH; Germany.
Glogauer et al.; The Role of Actin-binding Protein 280 in Integrin-dependent Mechanoprotection; Journal of Biological Chemistry; Jan. 16, 1998; pp. 1689-1698; vol. 273; No. 3.
Lo et al.; Cell Movement is Guided by the Rigidity of the Substrate; Biophysical Journal; Jul. 2000; pp. 144-152; vol. 79.
Henry et al.; Magnetic Anisotropy and Domain Patterns in Electrodeposited Cobalt Nanowires; European Physical Journal B; 2001; pp. 35-54; vol. 20.
Encinas-Oropesa et al; Dipolar Interactions in Arrays of Nickel Nanowires Studied by Ferromagnetic Resonance: American Physical Review B; Feb. 15, 2001; 6 pgs; Vo. 63; No. 10.
Balaban et al.; Force and Focal Adhesion Assembly: A Close Relationship Studied Using Elastic Micropatterned Substrates; Nature Cell Biology; May 2001; pp. 466-472; vol. 3.
Riveline et al.; Focal Contacts as Mechanosensors: Externally Applied Local Mechanical Force Induces Growth of Focal Contacts by an mDia1-dependent and ROCK-independent Mechanism; Journal of Cell Biology; Jun. 4, 2001; pp. 1175-1185; vol. 153; No. 6; Rockefeller University Press.
Geiger et al.; Transmembrane Extracellular Matrix—Cytoskeleton Crosstalk; Nature Reviews / Molecular Cell Biology; Nov. 2001; pp. 793-805; vol. 2; Macmillan Magazines Ltd.
Zimmermann et al.; Cardiac Grafting of Engineered Heart Tissue in Syngenic Rats; Circulation; 2002; pp. I151-I157; vol. 106; Suppl. I.
Beningo et al.; Flexible Substrata for the Detection of Cellular Traction Forces; Trends in Cell Biology; Feb. 2002; pp. 79-84; vol. 12; No. 2.
Alenghat et al.; Mechanotransduction: All Signals Point to Cytoskeleton, Matrix, and Integrins; Science's stke; Feb. 12, 2002; 5 pgs.
Kaverina et al.; Tensile Stress Stimulates Microtubule Outgrowth in Living Cells; Research Article; Journal of Cell Science; Mar. 21, 2002; pp. 2283-2291; vol. 115; No. 11.
Charras et al.; Single Cell Mechanotransduction and Its Modulation Analyzed by Atomic Force Microscope Indentation; Biophysical Journal; Jun. 2002; pp. 2970-2981; vol. 82
Galbraith et al.; The Relationship Between Force and Focal Complex Development; Journal of Cell Biology; Nov. 25, 2002; 695-705; vol. 159; No. 4.
Hu et al.; Intracellular Stress Tomography Reveals Stress Focusing and Structural Anisotropy in Cytoskeleton of Living Cells; American Journal of of Physical Cell Physiology; Jul. 2, 2003; pp. C1082-C1090; vol. 285.
Ingber; Mechanobiology and Diseases of Mechanotransduction; Annals of Medicine; 2003; pp. 564-577; vol. 35; No. 8.
Tan; Cells Lying on a Bed of Microneedles: An Approach to Isolate Mechanical Force; Proceedings of the National Academy of Sciences; Feb. 18, 2003; pp. 1484-1489; vol. 100; No. 4.
Hultgren et al.; Cell Manipulation Using Magnetic Nanowires; Journal of Applied Physics; May 9, 2003; pp. 7554-7556; vol. 93.
Tan et al.; Simple Approach to Micropattern Cells on Common Culture Substrates by Tuning Substrate Wettability; Tissue Engineering; 2004; pp. 865-872; vol. 10; No. 5/6.
Huang et al.; Cell Mechanics and Mechanotransduction: Pathways, Probes, and Physiology; American Journal of Physiology—Cell Physiology; 2004; 12 pgs.; vol. 287.
Wang et al.; Visualizing the Mechanical Activation of Src; Nature; May 21, 2005; pp. 1040-1045; vol. 434; Nature Publishing Group.
Du Roure et al.; Force Mapping in Epithelial Cell Migration; Proceedings of the National Academy of Sciences of the USA; Sep. 27, 2005; pp. 2390-2395; vol. 102; No. 7.
Noda et al.; A Shear Stress Sensor for Tactile Sensing with the Piezoresistive Cantilever Standing in Elastic Material; Sensors and Actuators A; 2006; pp. 295-301; vol. 127.
Discher et al.; Tissue Cells Feel and Respond to the Stiffness of Their Substrate; Science; Nov. 18, 2005; pp. 1139-1143; vol. 310.
Bershadsky et al.; Adhesion-Mediated Mechanosensitivity: A Time to Experiment, and a Time to Theorize; Current Opinion in Cell Biology; 2006; pp. 472-481; vol. 18.

(56) References Cited

OTHER PUBLICATIONS

Matthews et al.; Cellular Adaptation to Mechanical Stress: Role of Integrins, Rho, Cytoskeletal Tension and Mechanosensitive Ion Channels; Journal of Cell Science; 2006; pp. 508-518; vol. 119; The Company of Biologists.
Sniadecki et al.; Nanotechnology for Cell-Substrate Interactions; Annals of Biomedical Engineering; Jan. 2006; pp. 59-74; vol. 34; No. 1.
Giannone et al.; Substrate Rigidity and Force Define Form Through Tyrosine Phosphatase and Kinase Pathways; Trends in Cell Biology; Mar. 10, 2006; pp. 213-223; vol. 16; No. 4
Vogel et al.; Local Force and Geometry Sensing Regulate Cell Functions; Nature Reviews, Molecular Cell Biology; Apr. 2006; pp. 265-275; vol. 7.
Blumenfeld; Isostaticity and Controlled Force Transmission in the Cytoskeleton: A Model Awaiting Experimental Evidence; Biophysical Journal; Sep. 2006; pp. 1970-1983; vol. 91.
Lemmon et al.; Shear Force at the Cell-Matrix Interface: Enhanced Analysis for Microfabricated Post Array Detectors; Mechanics & Chemistry of Biosystems; Jun. 20, 2005; 22 pgs; vol. 2; No. 1.
Sniadecki et al.; Microfabricated Silicone Elastomeric Post Arrays for Measuring Traction Forces of Adherent Cells; Methods in Cell Biology; 2007; pp. 313-328; vol. 83.
Evans et al.; Magnetically Actuated Nanorod Arrays as Biomimetic Cilia; Nano Letters; Apr. 10, 2007; pp. 1428-1434; vol. 7; No. 5.
Sniadecki et al.; Magnetic Microposts as an Approach to Apply Forces to Living Cells; Proceedings of the National Academy of Sciences; Sep. 11, 2007; pp. 14553-14558; vol. 104; No. 37.
Coey; Magnetism and Magnetic Materials; 2010; 633 pgs; Cambridge University Press; Dublin.
Xi et al.; Comparison of Contractile Behavior of Native Murine Ventricular Tissue and Cardiomyocytes Derived from Embryonic or Induced Pluripotent Stem Cells; FASEB Journal; 2010; pp. 2739-2751; vol. 24.
Tulloch et al.; Growth of Engineered Human Myocardium With Mechanical Loading and Vascular Coculture; Circulation Research; 2011; pp. 47-59; vol. 109.
Mehta et al.; Pharmacological Response of Human Cardiomyocytes Derived from Virus-free Induced Pluripotent Stem Cells; Cardiovascular Research; May 12, 2011; pp. 577-586; vol. 91; European Society of Cardiology.
Schaaf et al.; Human Engineered Heart Tissue as a Versatile Tool in Basic Research and Preclinical Toxicology; PLoS One; Oct. 2011; 11 pgs; vol. 6; No. 10.
Boudou et al.; A Microfabricated Platform to Measure and Manipulate the Mechanics of Engineered Cardiac Microtissues; Tissue Engineering; 2012; pp. 910-919; vol. 18; Nos. 9/10.
Pillekamp et al.; Contractile Properties of Early Human Embryonic Stem Cell-Derived Cardiomyocytes: Beta-Adrenergic Stimulation Induces Positive Chronotropy and Lusitropy but Not Inotropy; Stem Cells and Development; 2012; pp. 2111-2121; vol. 21; No. 12.
Navarrete et al.; Screening Drug-Induced Arrhythmia Using Human Induced Pluripotent Stem Cell-Derived Cardiomyocytes and Low-Impedance Microelectrode Arrays; Circulation; Nov. 3, 2012; pp. S3-S13; vol. 128
Hein et al.; Fabrication of Bioinspired Inorganic Nanocilia Sensors; Transactions of Magnetics; Jan. 2013; pp. 191-196; vol. 49; No. 1.

Zhang et al.; Tissue-Engineered Cardiac Patch for Advanced Functional Maturation of Human ESC-derived Cardiomyocytes; Biomaterials; 2013; pp. 5813-5820; vol. 34.
Himmel; Drug-Induced Functional Cardiotoxicity Screening in Stem Cell-Derived Human and Mouse Cardiomyocytes: Effects of Reference Compounds; Journal of Pharmacological and Toxicological Methods; May 10, 2013; pp. 97-111; vol. 68.
Agarwal et al.; Microfluidic Heart on a Chip for Higher Throughput Pharmacological Studies; Lab on a Chip; Jun. 17, 2013; pp. 3599-3608; vol. 13; The Royal Society of Chemistry.
Hirt et al.; Cardiac Tissue Engineering; Circulation Research; 2013; pp. 354-367; vol. 113.
Yang et al.; Engineering Adolescence Maturation of Human Pluripotent Stem Cell-Derived Cardiomyocytes; Circulation Research; 2014; pp. 511-523; vol. 114.
Schaff et al.; Generation of Strip-Format Fibrin-Based Engineered Heart Tissue (EHT); Methods in Molecular Biology; 2014; pp. 121-129; vol. 1181.
Stoehr et al.; Automated Analysis of Contractile Force and $Ca^{2+}$ Transients in Engineered Heart Tissue; American Journal of Physiology-Heart and Circulatory Physiology; Feb. 28, 2014; pp. H1353-H1363; vol. 306.
Hayakawa et al.; Image-based Evaluation of Contraction-relaxation Kinetics of Human-induced Pluripotent Stem Cell-derived Cardiomyocytes: Correlation and Complementarity with Extracellular Electrophysiology; Journal of Molecular and Cellular Cardiology; Sep. 23, 2014; pp. 178-191; vol. 77.
Bhandari; Engineering a Novel Device to Implement Afterload on Human Stem Cell-Derived Cardiac Tissues; 2015; 73 pgs.
Kim et al.; Mechanism of Automaticity in Cardiomyocytes Derived from Human Induced Pluripotent Stem Cells; Journal of Molecular and Cellular Cardiology; Jan. 30, 2015; pp. 81-93; vol. 81.
Mathur et al.; Human iPSC-based Cardiac Microphysiological System for Drug Screening Applications; Scientific Reports; Mar. 9, 2015; 7 pgs; vol. 5.
Eder et al.; Human Engineered Heart Tissue as a Model System for Drug Testing; Advanced Drug Delivery Reviews; May 27, 2015; pp. 214-224; vol. 96.
Gilchrist et al.; High-throughput Cardiac Safety Evaluation and Multi-Parameter Arrhythmia Profiling of Cardiomyocytes Using Microelectrode Arrays; Toxicology and Applied Pharmacology; Jul. 29, 2015; pp. 249-257; vol. 288
Aung et al.; 3D Cardiac µtissues within a Microfluidic Device with Real-time Contractile Stress Readout; Lab on a Chip; Nov. 9, 2015; pp. 153-162; vol. 16.
Tzatzalos et al.; Engineered Heart Tissues and Induced Pluripotent Stem Cells: Macro- and Microstructures for Disease Modeling, Drug Screening, and Translational Studies; Advanced Drug Delivery Reviews; 2016; pp. 234-244; vol. 96.
Sniadecki et al.; Magnetic Method to determine Myocardial Tissue Forces; Unpublished U.S. Appl. No. 62/307,157, filed Mar. 11, 2016; 74 pgs.
Bielawski et al.; Real-Time Force and Frequency Analysis of Engineered Human Heart Tissue Derived from Induced Pluripotent Stem Cells Using Magnetic Sensing; Tissue Engineering Part C; Oct. 1, 2016; pp. 932-940; vol. 22; No. 10.

* cited by examiner

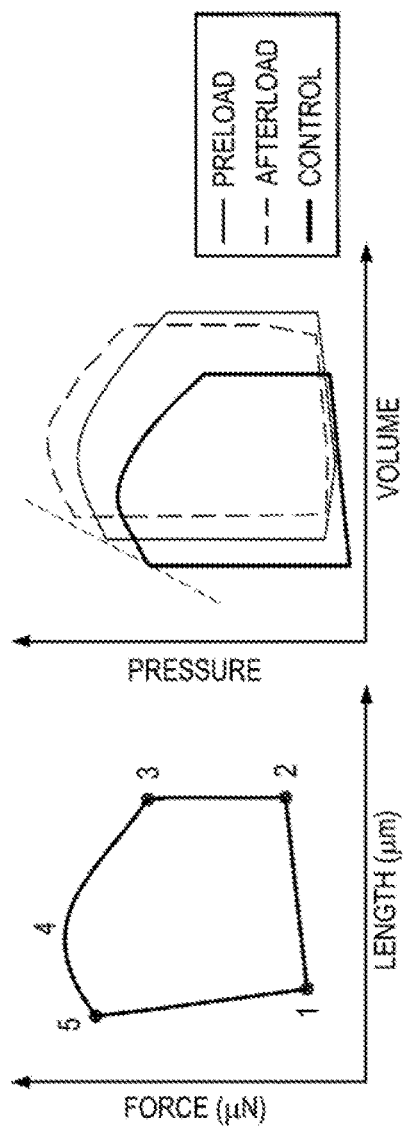
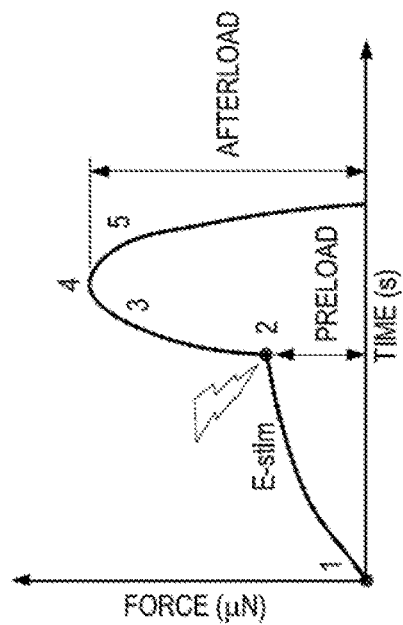
FIG. 4A  FIG. 4B  FIG. 4C ated signal corresponds to...

SYSTEM FOR MAGNETIC DETECTION OF MYOCARDIAL FORCES

CROSS-REFERENCE TO RELATED APPLICATIONS

This application claims the benefit of U.S. Provisional Application No. 62/307,157, filed Mar. 11, 2016, the disclosure of which is incorporated herein by reference in its entirety.

STATEMENT OF GOVERNMENT LICENSE RIGHTS

This invention was made with government support under Grant Nos. CBET-1509106 and CMMI-1402673, awarded by the National Science Foundation. The government has certain rights in the invention.

FIELD

This application relates to culturing and analysis of tissue and/or cells.

BACKGROUND

The heart can be loosely characterized as a positive displacement chamber that expands and contracts to cause blood to flow through the body. Heart contractions may occur with a frequency of approximately 1 Hz in a human subject. Abnormal frequency and/or forces associated with cardiomyocyte contraction may be indicative of disease. Cardiomyocyte tissues may be engineered and produced in a laboratory setting to investigate and study the forces and biology of the tissues. Such laboratory models may be useful in the formation of replacement tissues for therapeutic applications, as the heart does not have great ability to repair itself after infarctions. Engineered cardiac tissue may allow repair of the myocardium. Monitoring progress of cardiac cells and tissues for their force-generating capabilities may allow doctors and researchers to assess the maturity and viability of the cardiac cells and/or tissue, and thereby enhance the likelihood of successful repair.

SUMMARY

In various examples, systems and methods are provided for improved magnetic detection of myocardial forces of engineered cardiac cells and/or tissue.

In accordance with some embodiments of the present invention, cardiac tissue analysis devices are generally described. In some examples, the cardiac tissue analysis devices may comprise a base and a first post having a proximal end coupled to the base and a distal end. In some examples, the first post may comprise a first polymer and a magnetic portion. In various other examples, the cardiac tissue analysis devices may comprise a second post comprising a second polymer and having a proximal end coupled to the base and a distal end. The distal end of the second post may be separated from the distal end of the first post by a gap. In further examples, the cardiac tissue analysis devices may further comprise a magnetometer disposed proximate to the first post. In various examples, the magnetometer may be effective to generate a signal in response to a deflection of the distal end of the first post. In some other examples, the cardiac tissue analysis devices may comprise a filter circuit communicatively coupled to the magnetometer. In yet other examples the filter circuit may be effective to pass signals of a first frequency range. In various examples, the first frequency range may include frequencies associated with beating of cardiac tissue.

In accordance with some other embodiments of the present invention, methods of magnetically detecting forces in cardiac tissues are generally described. In some examples, the methods may include culturing cardiac tissue such that the cardiac tissue adheres to a first post and a second post. In yet other examples, the first post may comprise a first polymer and a magnetic portion and the second post may comprise a second polymer. In various other examples, the methods may further include, detecting, by a magnetometer situated proximate to the first post, a change in a magnetic field resulting from a deflection of the first post in a first direction from a first position to a second position. In still further examples, the methods may further comprise generating a signal corresponding to the change in the magnetic field. In still other examples, the methods may comprise filtering the signal by filtering out frequencies of the signal outside of a first frequency range to produce a filtered signal. In various cases, the first frequency range may include frequencies associated with beating of cardiac tissue. In other examples, the methods may further comprise determining a force exerted by the cardiac tissue based at least in part on the filtered signal.

In some examples, other methods of magnetically detecting forces in cardiac tissues are generally described. In some examples, the methods may comprise culturing cardiac tissue such that the cardiac tissue adheres to a first post and a second post. In various examples, the first post may comprise a first polymer and a magnetic portion and the second post may comprise a second polymer. In some further examples, the methods may further comprise positioning the first post and the second post in a well of a multi-well plate. In still other examples, the methods may further comprise adding a therapeutic agent to the well. In some further examples, the methods may comprise detecting, by a magnetometer situated proximate to the first post, changes in a magnetic field resulting from deflections of the first post due to beating of the cardiac tissue. In some other examples, the methods may further comprise generating a signal corresponding to the changes in the magnetic field over time. In yet other examples, the methods may further comprise filtering the signal by filtering out frequencies of the signal outside of a first frequency range to produce a filtered signal. In some cases, the first frequency range may include frequencies associated with beating of cardiac tissue. In various further examples, the methods may further comprise determining, based at least in part on the filtered signal, changes in force exerted by the cardiac tissue over time.

Still other embodiments of the present invention will become readily apparent to those skilled in the art from the following detailed description, wherein are described embodiments by way of illustrating the best mode contemplated for carrying out the invention. As will be realized, the invention is capable of other and different embodiments and its several details are capable of modifications in various obvious respects, all without departing from the spirit and the scope of the present invention. Accordingly, the drawings and detailed description are to be regarded as illustrative in nature and not as restrictive.

BRIEF DESCRIPTION OF DRAWINGS

FIG. 4A is a graph of preload and afterload forces varied over time with an external magnet, in accordance with various embodiments of the present disclosure.

FIG. 4B is a length-force graph of cardiac tissue in accordance with various embodiments of the present disclosure.

FIG. 4C is a graph exhibiting cardiac pressure-volume (PV) loops representing changes in pressure during preload and/or afterload in cardiac tissue, in accordance with various embodiments of the present disclosure.

DETAILED DESCRIPTION

Figure 1:
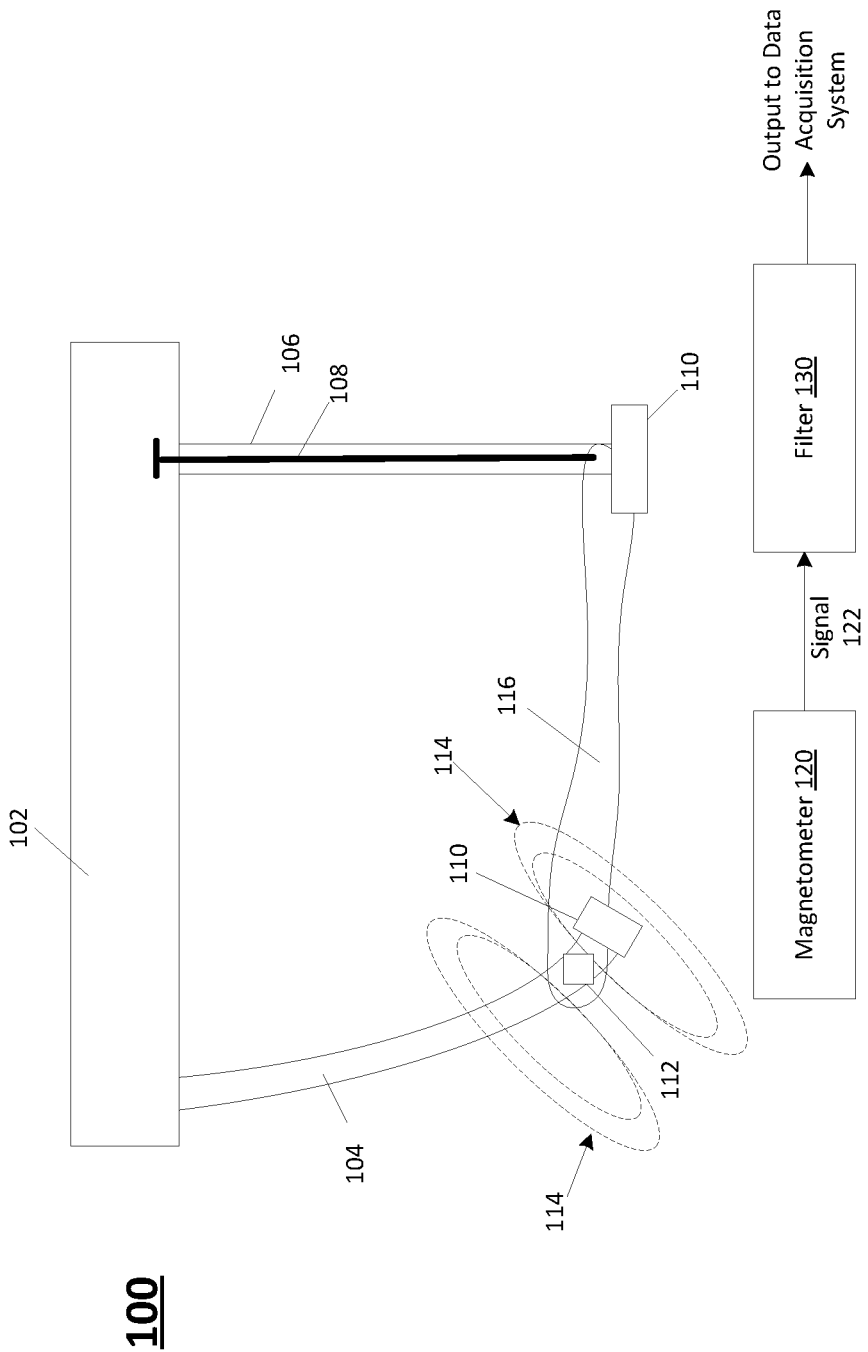
FIG. 1 depicts a side view of a device that can be used to magnetically detect myocardial forces, in accordance with various embodiments of the present disclosure.

In the following description, reference is made to the accompanying drawings that illustrate several embodiments of the present disclosure. It is to be understood that other embodiments may be utilized and system or process changes may be made without departing from the spirit and scope of the present disclosure. The following detailed description is not to be taken in a limiting sense, and the scope of the embodiments of the present invention is defined only by the claims of the issued patent. It is to be understood that drawings are not necessarily drawn to scale.

Various embodiments of the present disclosure provide improved systems and methods for magnetic detection and determination of myocardial forces of engineered cardiac cells and/or tissue. These embodiments may improve a signal to noise ratio for determination of myocardial forces. Additionally, these embodiments may reduce data storage requirements for myocardial force detection and determination, relative to optical methods of monitoring the tissue. The magnetic detection and filtering techniques described herein allow for repeatable, accurate, and precise results. As used herein, "cardiac tissue" and/or "myocardial tissue" may refer to single cardiomyocytes and/or multiple cardiomyocytes fused to form a tissue. In the following detailed description these terms may sometimes be used interchangeably.

In some examples, single cardiomyocytes may be cultured and affixed to polymeric microposts, sometimes referred to herein as "posts". The force response of single cardiomyocytes can provide information about the effects of a variety of reagents and treatments to which the cardiomyocytes are exposed as well as information about the development and maturity of the cardiomyocytes. In various examples, small tissues made up of cardiomyocytes may be cultured and attached between microposts. The cardiomyocytes may be seeded within a fiber matrix. In some examples, the fiber matrix may comprise collagen, fibrin, matrigel, silicone, and/or other polymeric substances. At least some of the microposts to which the cardiac tissue is affixed may be designed in such a way as to be flexible. In various examples, the diameter, length, or material of the microposts may be selected in order to impart a desired flexibility or rigidity to the microposts. The cardiac tissue may be effective to bend the flexible microposts upon contraction of the cardiac tissue. In this disclosure, microposts may sometimes be referred to as "posts". Additionally, in some cases, the posts described herein may have a wide variety of dimensions. As such, the prefix "micro" used in conjunction with the term "posts" does not describe all possible and intended posts contemplated by the present disclosure. As described in further detail below, the force generated by the cardiac tissue may be determined based on the amount by which the post is bent or deflected.

Previous attempts at seeding cardiac tissue and monitoring forces from engineered heart tissues have encountered a variety of obstacles. For example, sophisticated image analysis may be used to monitor the motion of the microposts to which the cardiac tissue is affixed. The force exerted by the cardiac tissue may be determined based on the motion; however, a dedicated microscope and highly complex computer vision techniques are required to monitor the force of the cardiac tissue over time. The computer processing requirements and data storage requirements for processing and storing the optical data is relatively high, especially as compared with the techniques described herein. Additionally, expansion beyond a single 24 well plate requires additional microscopes and/or a significant set-up and tear-down time for each point of force measurement. As such, massively parallel studies using such techniques may be prohibitively expensive and/or time consuming. Some other methods of monitoring the force development of engineered cardiomyocyte tissues require destructive methods or merely monitor the electrophysiology and not the actual force generation of the cardiac tissue.

FIG. 1 depicts a side view of a device 100 that can be used to magnetically detect myocardial forces, in accordance with various embodiments of the present disclosure. Device 100 may include a base 102 and a plurality of posts including, for example, post 104 and post 106. In some examples, posts 104 and/or 106 may comprise a polydimethylsiloxane (PDMS) polymer. In various examples, the PDMS polymer may be formed from a four-part acrylic mold or another mold. In various examples, base 102 may be comprised of a biocompatible matrix material such as collagen, fibrin, Matrigel, and/or any other suitable material to which to couple and/or affix microposts. Although two posts 104 and 106 are depicted in FIG. 1, any number of posts may be used in accordance with various embodiments of the present disclosure. In some examples, there may be a gap of between 4 and 20 millimeters between adjacent posts, such as posts 104 and 106. In some further examples, posts 104 and 106 may be between approximately 5 mm and 24 mm tall and between 0.5 mm and 3 mm in diameter.

In other examples, posts may be taller or shorter and may have larger or smaller diameters relative to the ranges previously mentioned, according to the desired implementation. Similarly, the gaps between posts may in some cases be smaller than 4 millimeters, depending on the desired implementation. As is described in further detail below, the dimensions of the posts may be selected in order to impart rigidity and/or flexibility to the posts. In some examples, posts arranged in an array may be spaced for insertion into a multi-well plate such as, for example, a 24-well plate. In various examples, each pair of posts, such as posts 104 and 106, in an array of posts may be appropriately spaced and located such that each pair of posts may correspond with and fit into a well of a multi-well plate.

The base 102 may be rigid or flexible and may be designed to interface with a 24-well or other-numbered well plate so that the tips 110 of pairs of posts (e.g., posts 104 and 106) of base 102 may be inverted to fit into individual wells of the plate. Cardiac tissue 116 may be cultured and may adhere to tips 110 of the posts 104, 106 such that the cardiac tissue grows "between" the two posts. For example, cardiac tissue 116 depicted in FIG. 1 may adhere to posts 104 and 106 and may be grown between the two posts. In some examples, cardiac tissue 116 may be cultured in the individual wells. In various other examples, and as described in further detail below, wells of a multi-well plate into which tips 110 of posts 104, 106 are inserted may include solutions comprising nutrients and/or therapeutic agents. In some examples, cardiac tissue adhered to posts 104, 106 may be exposed to therapeutic agents in order to test the efficacy of the therapeutic agents by measuring the response of the cardiac tissue to the agents.

A first proximal end of posts 104 and 106 may be coupled to base 102 and a second, distal end of posts 104 and 106 may comprise a tip 110. While in some examples the tip 110 may be non-uniform relative to the remainder of the posts in order to promote tissue attachment, in various other examples, the tip 110 may be relatively uniform with respect to the post, depending on the desired implementation. In various examples, the posts may comprise a polymeric material and may be less than about 2 millimeters in diameter. Post 104 may be sufficiently flexible such that the tip 110 of post 104 may be deflected away from an at-rest position in response to the contraction of cardiac tissue attached to post 104. For example, cardiac tissue 116 may be attached to post 104 at or near tip 110 of post 104. Cardiac tissue 116 may also be attached to post 106, or another post and/or object. When cardiac tissue 116 contracts due to the spontaneous beating of cardiac tissue, the force of the contraction causes post 104 to bend or deflect from an at-rest position to a second, deflected position. In FIG. 1, post 104 is shown in a deflected position, bent away from a vertical rest position. Post 106 may include a rigid insert 108 to impart rigidity to post 106 in order to prevent and/or limit the deflection or other movement of post 106 from the vertical rest position in response to the contraction of cardiac tissue 116. Rigid insert 108 may comprise silicon glass, metal, plastic and/or any other material of sufficient rigidity to prevent and/or reduce the deflection of post 106 during the contraction of cardiac tissue 116.

In some other examples, post 106 may not include a rigid insert and may accordingly exhibit similar flexibility as other posts attached to base 102. In still other examples, the diameter and/or length of posts may be altered in order to impart the desired level of flexibility to various posts. For example, if it is desired that some posts be more flexible and other posts be less flexible, some posts may be formed with a smaller diameter and/or a greater length in order to impart greater flexibility along the length of the post. Similarly, other posts may be formed with a larger diameter and/or a shorter length in order to impart rigidity/limit flexibility. Additionally, although the description herein refers to posts of a cylindrical shape, posts may instead be formed with other shapes. For example, the posts may be formed in a parallelepiped shape or other polygonal shape.

As depicted in FIG. 1, post 104 may comprise a magnetic material 112 such as neodymium and/or another magnet embedded within or otherwise coupled to the post. In some examples, tip 110 of post 104 may be effective to prevent the post 104 from tearing due to the embedding of magnetic material 112. In various further examples the magnetic material may be smaller than 2 mm$^3$. In various examples, the magnetic material 112 may be disposed at or near the tip of post 104 such that when post 104 is deflected the magnet is accordingly displaced from a first position to a second position by the deflection of the post 104. Magnetic material 112 produces a magnetic field 114. Deflection of post 104 may cause magnetic material 112 to be displaced and to rotate relative to the original position of magnetic material 112. Accordingly, the magnetic field 114 associated with magnetic material 112 may similarly translate and rotate due to the translation and rotation of magnetic material 112. A magnetometer 120 disposed proximate to post 104 may detect the changes in the strength of a detected magnetic field as the magnetic material 112 and magnetic fields 114 move closer to and away from the magnetometer 120 with the beating of the cardiac tissue 116. The magnetometer 120 may be disposed at various positions relative to positions of post 104 and post 106. Magnetometer 120 may be positioned such that magnetometer 120 can detect a change in the magnetic field due to deflection of magnetic material 112 from a first position to a second position. In various examples, magnetometer 120 may be positioned within 0.1-10 millimeters from post 104. In some other examples, magnetometer 120 may be positioned between 11-30 millimeters from post 104. In various other examples, magnetometer 120 may be positioned closer to or further from post 104, depending on the type of magnetometer and/or the type of magnetic material used.

In some examples, the change in magnetic field strength detected by the magnetometer 120 may be on the order of microteslas and may affect only a local region within the well in which posts 104 and 106 are disposed. Accordingly, magnetic field changes associated with the beating of cardiac tissue 116 may be distinguished from magnetic field changes associated with beating of cardiac tissue adhered to other posts, and/or disposed in other wells of a multi-well plate.

In various examples the magnetometer 120 may be a giant magnetoresistive (GMR) sensor. In some examples, an array of magnetometers 120 may be arranged such that a single magnetometer may be associated with each well of a multi-well plate. Accordingly, the changes in magnetic field strength associated with the cardiac tissue disposed in each well of a multi-well plate may be detected and distinguished from other wells. The change in field strength results in an output signal 122. The output signal 122 may comprise a voltage output from magnetometer 120.

In various examples, magnetometers and/or arrays of magnetometers may be arranged on printed circuit boards along with other circuitry for filtering and/or amplifying output signal 122. In some examples where magnetometers 120 are GMR-based magnetic sensors, the magnetometers 120 may include resistances arranged in a Wheatstone bridge configuration that results in a decrease in voltage of signal 122 when the magnetic field detected by the GMR sensor increases. Each measurement from the Wheatstone bridge of the GMR sensor may be output to as signal 122 to a high pass filter and/or a bandpass filter and amplified using one or more operational and/or instrumentation amplifiers. See, for example, FIG. 2 depicting an example of circuitry including magnetometer 120, filter 130 (a high pass filter in FIG. 2), and an instrumentation amplifier 220.

The output voltage from filter 130 may be detected by a data acquisition system and may be used to determine a force associated with the beating of the cardiac tissue 116, as discussed in further detail below. Although a high pass filter is depicted in the example circuitry shown in FIG. 2, in some other examples, low pass and/or bandpass filters may be used, in accordance with the various embodiments described herein, depending on the desired frequencies to be captured and passed to the data acquisition system.

Magnetometers 120 may be soldered to printed circuit boards containing conditioning circuitry. In some examples, the magnetometers 120 may comprise Wheatstone bridge configurations and may be routed to high-pass filters to reduce long-term drift of the system. Filters, such as the high pass filter 130 depicted in FIG. 2, may be designed to have a cut-off frequency that passes cardiac tissue contraction frequencies while excluding low-frequency ambient noise. In some examples, high pass filters 130 may have a cut-off frequency of approximately 0.01-0.3 Hz. In various other examples, high pass filters 130 may have a cut-off frequency of approximately 0.1-0.25 Hz. In still other examples high pass filters 130 may have a cut-off frequency of approximately 0.16 Hz-0.5 Hz. Although, various frequency ranges are provided for illustrative purposes, other ranges of cut-off frequencies may be used in accordance with the present disclosure. Identification of the frequency of rhythmic beating of the cardiac tissue can, in some examples, serve as an upper limit for the cutoff frequency of the high pass filters, although often a lower cut-off frequency may be used in order to avoid data loss from slower than average beating of cardiac tissue. Additionally, band pass and/or low pass filters may be used in various implementations in order to filter out frequencies lower than and/or higher than the frequencies associated with the beating of the cardiac tissue. Filter 130 may be effective to offset drift in the detected signals due to temperature fluctuations and/or due to ambient magnetic fields of the environment in which device 100 is situated.

Figure 2:
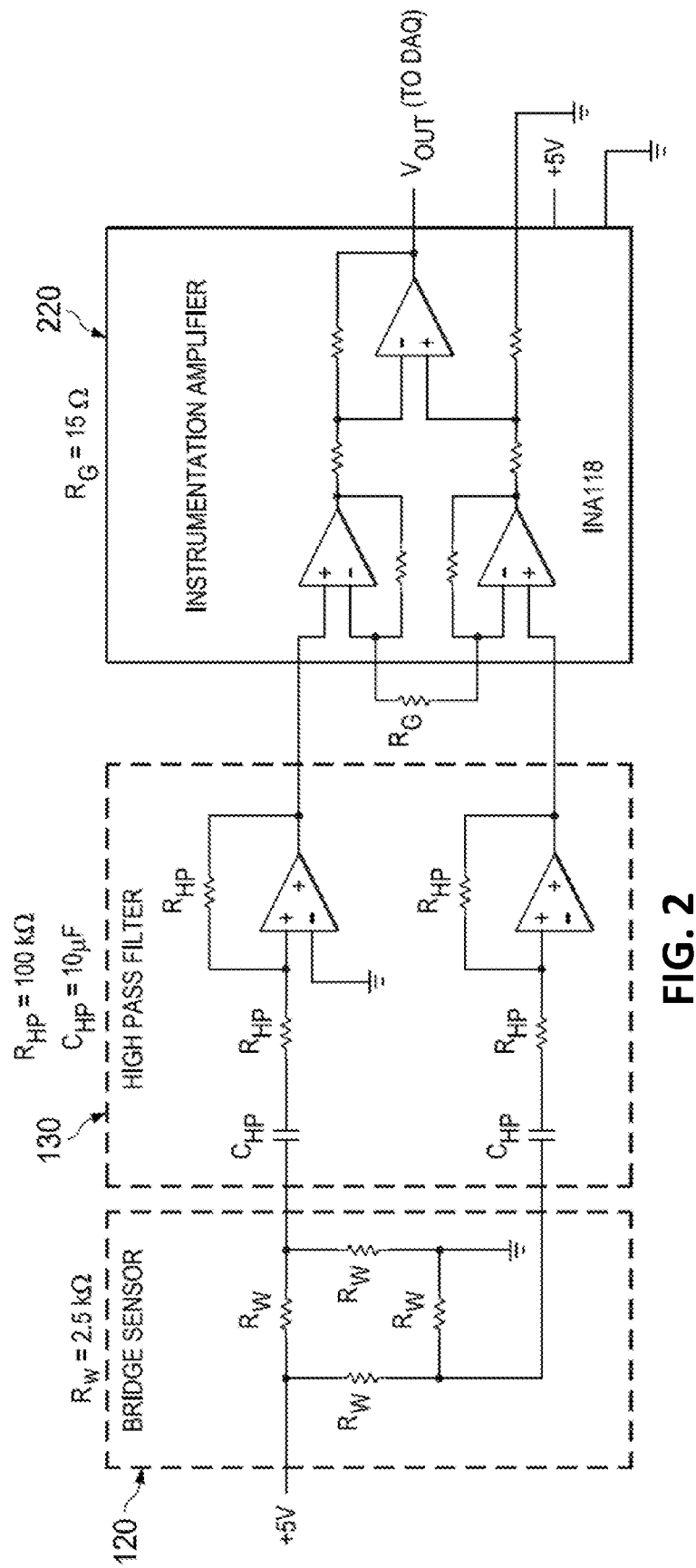
FIG. 2 depicts magnetometer circuitry for detecting a change in a magnetic field associated with beating of cardiac tissue and for filtering and amplifying a signal received from the magnetometer, in accordance with various embodiments of the present disclosure.

Signals from filters 130 may be routed through instrumentation amplifiers such as instrumentation amplifier 220 depicted in FIG. 2 before going through a data acquisition system. The data acquisition system may be effective to monitor and record the frequencies of cardiac tissue contraction and force. In addition, the data acquisition system may record the timing of additions of fluids, such as therapeutic agents and/or nutrients. The data acquisition system may include one or more processing elements and/or one or more memories effective to store data received from filter 130 depicted in FIG. 1.

Magnetic Model

The examples below describe experimental methods used to validate a system for magnetic detection of myocardial forces. Although particular data and instrumentation are described in the discussion below, other instruments (e.g., magnets, filters, materials) may be used in accordance with the present disclosure and such other instruments may yield different values than those discussed below for purposes of example.

A model of the system was developed in Matlab (although any suitable programming language may be used) by treating the embedded magnetic material 112 as a point dipole. A point dipole may be a fair approximation for the magnetic material 112, as the distance between the magnetic material 112 and the magnetometer 120 was much greater than the size of the magnetic material 112. In some examples, the dipole strength of 1 mm³ neodymium magnets may have a dipole strength of $M=7.5e_x+1.5e_y+1.5e_z$ mAm². The x-component of the stray field was determined for an array on the plane of the sensor to determine the effect of adjacent posts as well as the optimal location for the sensor. The projection was determined based on the magnetic field of a point dipole:

$$B = \frac{\mu_0}{4\pi}\left[3\frac{(m \cdot r)r}{r^5} - \frac{m}{r^3}\right] \quad (1)$$

where m is the magnetic moment described above, B is the magnetic field change, and r is the distance from the current location of the magnet to the position in the plane of the sensor. Due to the physical constraints of the system, the closest the sensor can be to the magnet in the vertical direction is 10 mm. In various examples, an optimum position of the magnetometer 120 relative to the post 104 may comprise locating magnetometer 120 a few millimeters ahead of the post 104.

The magnetic field change B can be used to determine the force of the tissues after a calibration is performed on the system. The force exerted by the cardiac tissue on the flexible post 104 is directly proportional to the distance the tip 110 of the flexible post 104 moves, determined by the stiffness and dimensions of the flexible post 104. The distance the tip 110 of the flexible post 104 moves causes a change in B at the magnetometer 120, which in turn creates a difference in the voltage read at a computing device. A calibration can be performed by manually moving the tips of the posts a specified distance (thus generating a known force) and monitoring the corresponding voltage change in the system. The voltage change is due to the B field change.

Magnetometers 120 may be spaced in an array such that adjacent magnetometers 120 do not have measurable signals when posts are deflected up to 300 μm. The orientation relative to the earth was found to slightly alter the response of the sensors, which is likely due to a move away from the linear range of the sensors while the earth's magnetic field was oriented against the stray magnetic field of the post. The sensors had a linear voltage-position response in multiple orientations with slightly different sensitivities.

Frequency and Force Plotting

In testing the system, voltage outputs from six sensors simultaneously tracked the active force generation of the posts in the first row of a 24-well plate. Data was recorded using LabView and displayed on screen in real-time during experiments. Post-hoc analysis was performed on all experiments to assess the frequency and magnitude of pulses over time. The data was filtered with a low-pass filter to remove measurement noise using an 8th order Butterworth filter with a cut off frequency of 7 Hz. Only the peak-to-peak amplitudes were recorded, so the mean was removed from the data. An exponential moving average filter with alpha=0.0001 was used to eliminate the means of the data and account for any low-frequency drift in the system that was not eliminated with the analogue high-pass filters.

After filtering the data, a custom peak finding program found the maximums and minimums of the data with a minimum amplitude of 7 mV, or about 5-10% of the typical baseline motion. Frequency was determined based on the time between maximums. The instantaneous magnitude was determined by subtracting the maximum from the adjacent minimum as long as the maximum and minimum were within two seconds of each other. Data was then grouped together for analysis with 30 seconds grouped at a time. The means of the frequency and magnitudes were averaged over each 30 second period until the end of the experiment at 180 seconds. In order to reduce errors due to slight adjustment of the posts during fluid addition, a four-second window around each fluid addition time point was removed from the averages for both the frequency and magnitude measurements.

Pharmacological Inhibitors

In various examples, cardiac tissues adhered to posts and disposed within wells of a multi-well plate may be exposed to therapeutic agents. For example, inhibition experiments may be performed using verapamil hydrochloride (CAS 152-11-4, Tocris Bioscience, Bristol, UK) and isoproterenol hydrochloride (CAS 5984-95-2, Sigma-Aldrich, St. Louis, Mo.). Cardiac tissues may be treated with a mixture of the relevant drug and deionized water. Therapeutic agents may be filtered and portioned into the appropriate dilution based on the final concentration. In some example experiments, some wells may serve as controls having no therapeutic agents.

Figure 3:
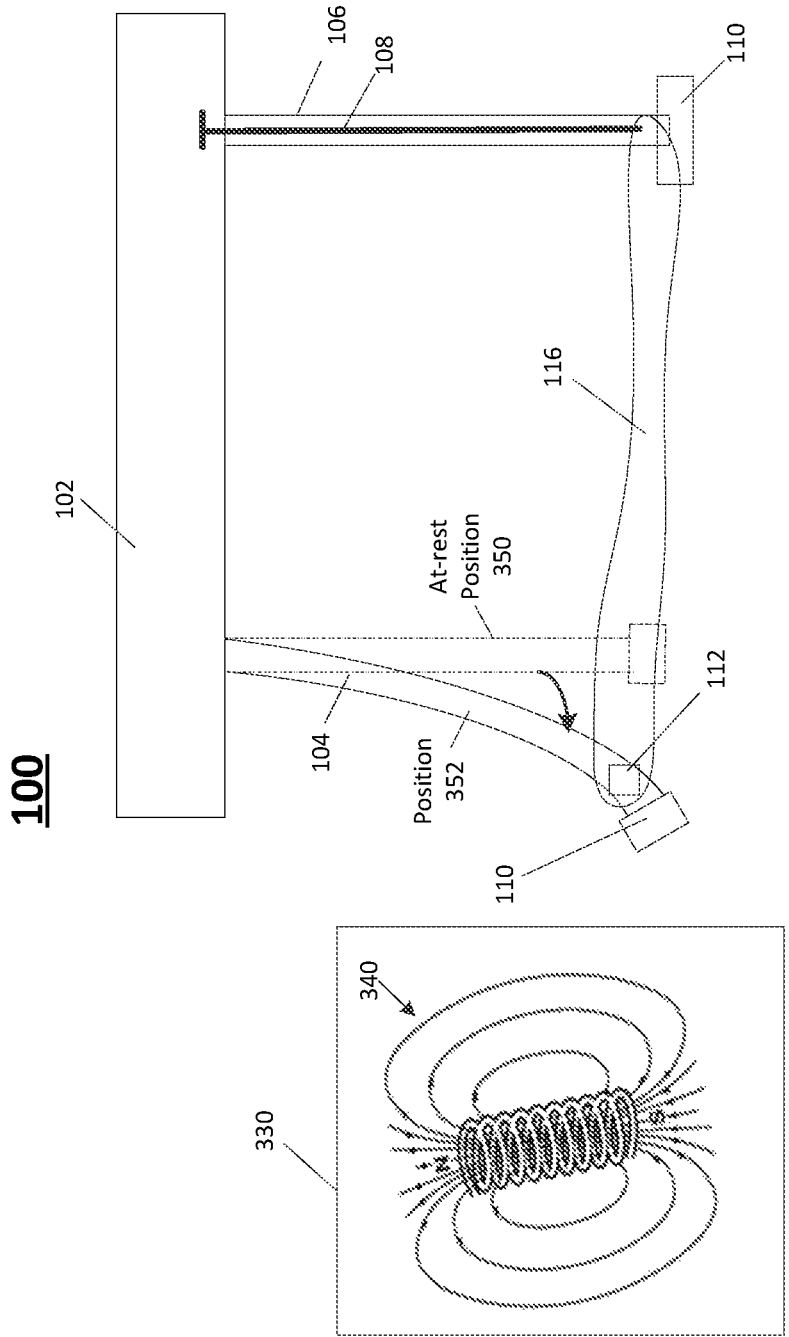
FIG. 3 depicts the example device of FIG. 1 including external magnets used to simulate preload and afterload of cardiac tissues, in accordance with various embodiments of the present disclosure.

FIG. 3 depicts the example device of FIG. 1 including an external magnet 330 used to simulate preload and afterload in cardiac tissues, in accordance with various embodiments of the present disclosure.

External magnetic fields may be applied to posts 104 and 106 of device 100 via an external magnet 330. In some examples, external magnet 330 may comprise a permanent magnet, while in other examples, external magnet 330 may comprise an electromagnetic coil 340 to impart a magnetic force that acts on the magnetic material 112 and pulls against the cardiac tissue 116 attached to post 104 and/or 106. In some examples, external magnet 330 may be disposed adjacent to post 104 and/or post 106. External magnet 330 may be effective to attract magnetic material 112 with a first force and thereby displace a distal end of post 104. When the cardiac tissue 116 relaxes during diastole, the restoring force of the post (e.g., a flexible post 104) causes the cardiac tissue 116 to stretch like the elastic recoil of the myocardium. However, when a magnetic force is applied, the cardiac tissue 116 is stretched further, similar to ventricular expansion during diastolic filling (sometimes referred to as "preload"). Accordingly, the cardiac tissue 116 may be strained by a first amount during and/or just after diastole of the cardiac cycle to stress the cardiac tissue 116 in order to simulate preload. For example, a flexible post 104 to which cardiac tissue 116 is adhered to may stretch from an at-rest position 350 to a position 352 due to the magnetic force from external magnet 330 attracting magnetic material 112. When cardiac tissue 116 begins to contract forcibly with electrical stimulation, and at the same time an increase in the magnetic force from external magnet 330 is applied, there is increased resistance to shortening akin to the resistance due to blood pressure during systole (sometimes referred to as "afterload"). Increasing preload and afterload can be done independently and with complex patterns by, for example, controlling the current running through the electromagnetic coil 340 at various points during the cardiac cycle of cardiac tissue 116 or by varying the distance between an external magnet 330 and magnetic material 112 (e.g., FIG. 4A). Using this pattern, the cardiac tissue's length-force (e.g., FIG. 4B) can be compared to cardiac pressure-volume (PV) loops for increasing preload and/or afterload (e.g., FIG. 4C). Thus, preload can be gradually increased to mimic increasing venous return and afterload to mimic increasing blood pressure during development, and change their loading conditions to mimic PV loops of heart failure or hypertension. In various examples, the amount of magnetic force applied to the magnetic material 112 may be modulated by changing an amount of current supplied to the electromagnetic coil 340.

Magnetic Sensors

Figure 5:
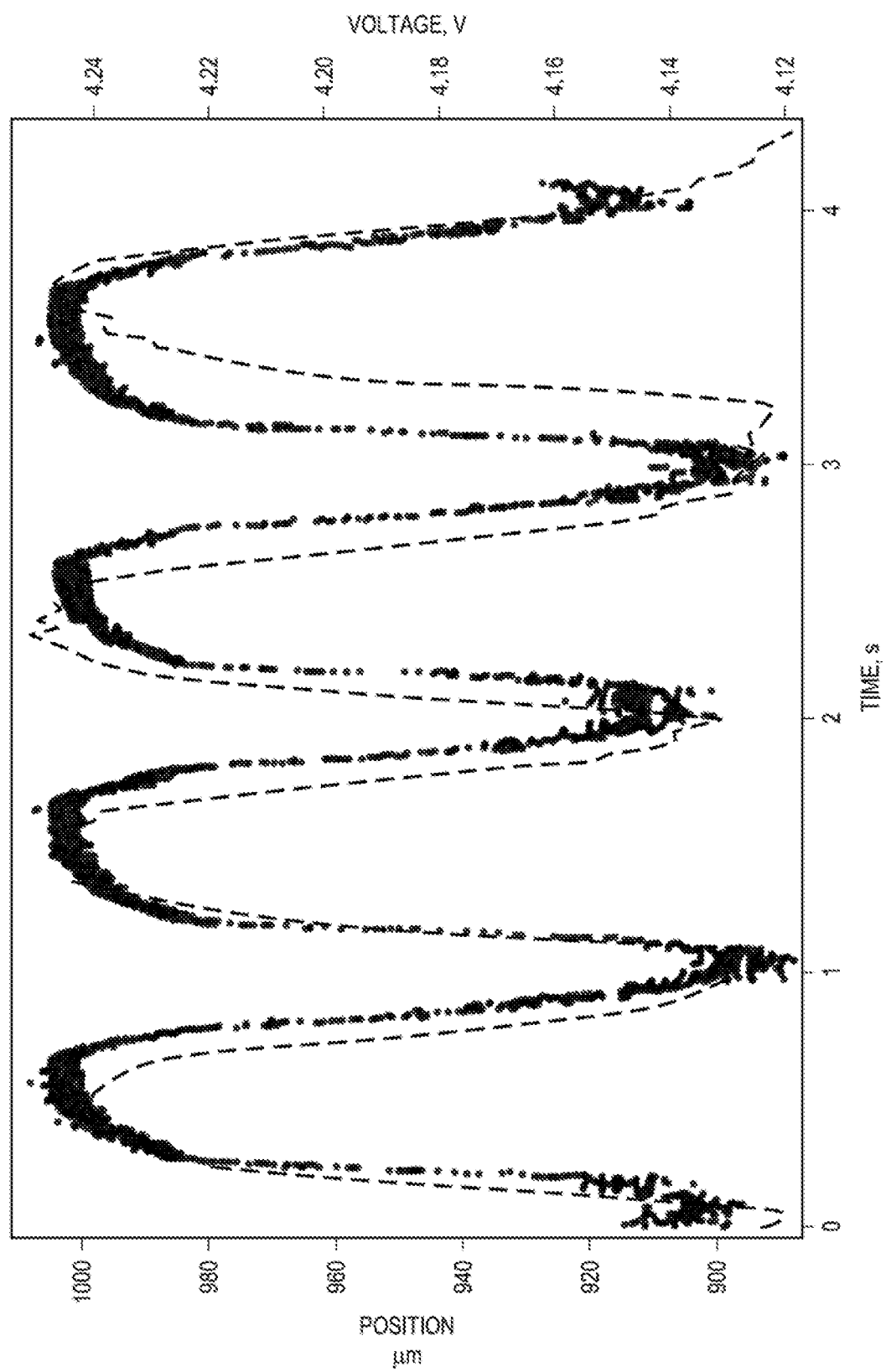
FIG. 5 is a graph showing varying post position and resulting voltage resulting from the beating of cardiac tissue in the various systems for magnetic detection of myocardial forces described in the present disclosure.

In various examples, high-speed optical microscopy may be used to track post deflections, but such an approach may have low throughput: one sample/well at a time. Additionally optical techniques may require a large amount of processing resources and data storage as well as expensive optical equipment. Moreover, the image analysis algorithms are cumbersome and require user-input to ensure accuracy of results. Accordingly, the magnetic approach described herein may be used to record the post deflections using giant magnetoresistive (GMR) sensors and/or other magnetometers (e.g., magnetometer 120 depicted in FIG. 1). Arrays of GMR sensors and/or other magnetometers may be used, with high pass filters and instrumentation amplifiers for signal processing to allow for parallel processing of multiple multi-well plates. When cardiac tissue 116 pulls on a flexible post (e.g., post 104 from FIG. 1), its movement causes the neodymium magnet or other magnetic material 112 to rotate and translate which, in turn, changes the strength of the magnetic field at the GMR sensor. The change in the field is very small (microteslas) and affects only a local region within its well, and not at the other wells. The field change results in a change in voltage output from the sensor, which can be calibrated to correspond to the post deflection detected using optical microscopy, and the corresponding contractile force (see FIG. 5). The voltage signal may be used to determine the force exerted by the cardiac tissue 116. Thus, real-time analysis of cardiac tissue contractions is possible without requiring powerful processing and large amounts of data storage. In various examples, a PID controller may be used in conjunction with the electromagnetic coil 340 (FIG. 3) to modulate preload and afterload in response to contractile forces of the cardiac tissue 116.

Preload Effect on Maturation in Cardiac Tissue

The following description describes an experiment to simulate preload effect on cultured cardiac tissue in the system for magnetic detection of myocardial forces described herein. The values described below may be altered in different implementations according to the desired strain to be introduced to the cardiac tissue.

Engineered heart tissues may be cultured as previous described, but with minor modifications in order to incorporate the neodymium magnet in the flexible posts. Briefly, $4 \times 10^5$ hiPSC-CMs (cardiomyocytes) may be mixed with $2 \times 10^5$ normal human dermal fibroblasts (a ratio previously optimized) in a fibrin scaffold. Constructs may be allowed to equilibrate for 7 days in order to form a tissue, or until spontaneous beating is observed. From this point on, tissues may be paced at 2 Hz. In this example, the target for preload (circumferential) stretch is based on previous measurements of human LV chamber dimensions during gestation. With electrical stimulation (2 Hz), cardiac tissue may be subjected to continuously increasing magnetic fields of 2% per day over two weeks. This will result in approximately 30% strain, which may be held for an additional 1 week. Strain will be achieved by the applied magnetic field produced by current driven through an electromagnetic coil 340 (FIG. 3), as previously described, and monitored with the GMR sensors, such as magnetometer 120 depicted in FIG. 1. Using a 24-well format, preload experiments MAY be run in parallel to examine a preload stretch range of 0% to 40% after two weeks.

After conditioning the cardiac tissue with preload, constructs may be fixed and cryo-sectioned for immunohistochemistry to assess their survival and maturation. Constructs may be assessed for proliferation and apoptosis levels, cell size and elongation, myofibril structure (sarcomere spacing and Z-band width by α-actinin), junctional integrity (N-cadherin, connexin-43), T-tubule formation (caveolin-3), β-myosin switching, expression of cTnI and ssTnI (described in Aim 1c.2), electrical maturation (KCNJ2), and ventricular phenotype (MLC2V). Reporter cell lines may be tested for maturation due to preload as they become available from the Allen Institute.

Contractile performance may be assessed biomechanically and conduction velocity assessed via $Ca^{2+}$ imaging (hiPSC-CMs expressing GCaMP6 or Fluo-4). Dynamics of force, velocity, and power may be assessed for constructs as described. Force-length analysis may be conducted in situ by applying magnetically-induced strain on constructs while measuring forces to obtain Frank-Starling curves (end-systolic elastance) and passive stiffness (end-diastolic elastance; FIG. 1G). Frequency-dependent gain in contractility and kinetics may also be assessed using electrical pacing from 0.5 to 3 Hz (force-Hz response).

Afterload Effect on Maturation in Cardiac Tissue

The following description describes an experiment to simulate afterload effect on cultured cardiac tissue in the system for magnetic detection of myocardial forces described herein. The values described below may be altered in different implementations according to the desired strain to be introduced to the cardiac tissue.

Systolic circumferential tension (afterload) may be estimated on a mid-wall human fetal muscle fiber using published data for LV dimensions and systolic blood pressure during gestation and analysis using Lame's equation. Such an analysis reveals that afterload increases linearly from 2.3 kPa to 8.2 kPa between 10 and 40 weeks. Thus, afterload may be tuned to recapitulate this dynamic range for initial experiments. The PID controller may be used to ensure that the afterload is not overdriven and to prevent the shortening of cardiac tissue. Cardiac tissue cultured on the posts without applied preload or afterload can contract with an active force up to 500 μN after 3 weeks. This converts to a longitudinal stress of 2.5 kPa (using an average tissue cross section value of $0.2\ mm^2$), which is equivalent in magnitude to the tension due to afterload at 10 weeks. The procedure may begin with zero afterload and may be progressively increased at a rate of 120 μN per day over two weeks. This may result in approximately 1650 μN, which can be held for an additional week. Using a 24-well format, afterload experiments may be run in parallel to examine a range of forces 70% below and 20% above the target of 1650 μN. The survival and maturation of constructs may be assessed as described above. Functional assessment may also be performed for conduction velocities, twitch force, velocity, and power, force-length response, force-frequency response, and tissue elasticity.

Bioreactor for Combined Preload and Afterload Creep

Since both preload and afterload are continually changing during fetal development, i.e. creep, a combination of preload and afterload may be applied that produces a force-length loop resembling the pressure-volume loops that promote cardiac hypertrophy (FIG. 4C). Using 24-well plates, each cardiac tissue disposed between two microposts may be given a different ratio of preload and afterload. Preload stretch may be increased progressively by 2% and afterload tension increased by 120 μN per day over two weeks. Afterwards, constructs may be assessed for hallmarks of maturation and improved contractile function as described above. Additionally, the combined biomechanical loading may be assessed with a thyroid hormone, triiodothyronine, or the Let-7 transgene on hiPSC-CM maturation and contractile performance.

Although in the description above, cardiac tissue is generally described as being cultured between the posts of device 100 (FIG. 1), in various other examples, different tissues may be used in accordance with the present disclosure. For example, other tissues that exhibit a rhythmic contraction may be studied using the systems for magnetic detection of forces described herein. In some examples, the systems described in the present disclosure are optimal for detecting and determining forces related to the rhythmic beating of cardiac tissue, as cardiac tissue contracts with a relatively stable frequency. As such, electronic filtering may be employed to filter out noise while capturing the signal of interest.

Figure 6:
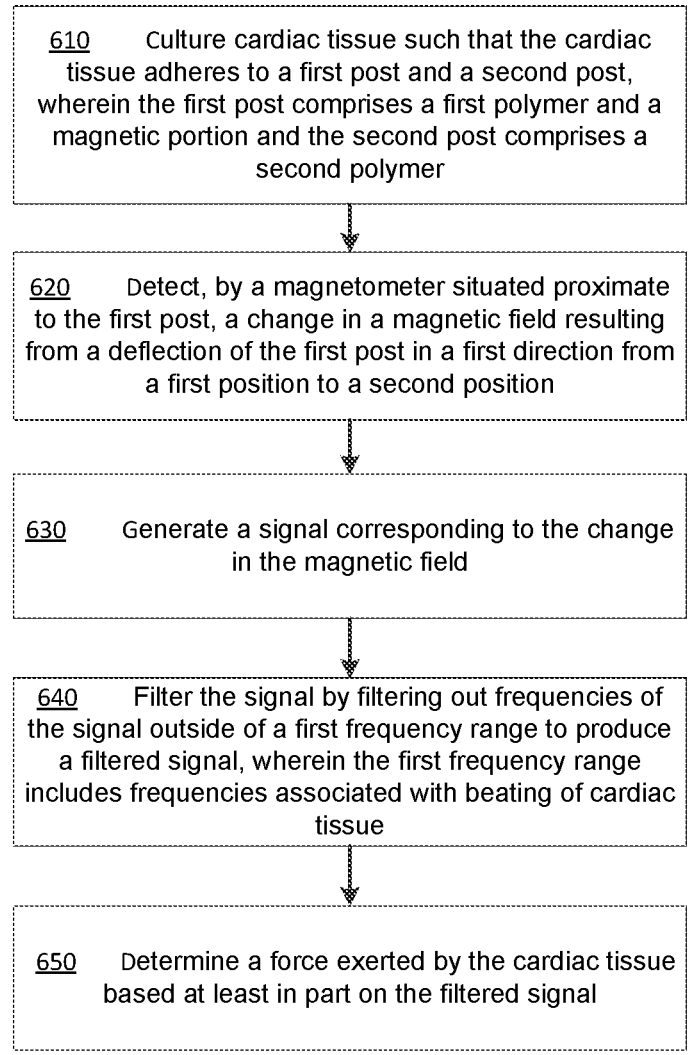
FIG. 6 depicts an example process for magnetically determining force exerted by cultured cardiac tissue, in accordance with various aspects of the present disclosure.

FIG. 6 depicts an example process for magnetically determining force exerted by cultured cardiac tissue, in accordance with various aspects of the present disclosure. Those portions of FIG. 6 that have been described previously with respect to FIGS. 1-5 may not be described again for purposes of clarity and brevity.

The process in FIG. 6 may begin at action 610, "Culture cardiac tissue such that the cardiac tissue adheres to a first post and a second post, wherein the first post comprises a first polymer and a magnetic portion and the second post comprises a second polymer". At action 810 cardiac tissue may be cultured in such a way that the tissue adheres to a first and a second post. As described above, in some cases the first post may be relatively flexible so as to bend under the force exerted by the cardiac tissue during contraction. Further, in some cases the second post may be relatively rigid so as not to deflect, or so as to minimize deflection during contractions of the cardiac tissue. In some further examples, rigidity may be imparted to the second post by inserted a rigid insert within the second post. For example, a silica, glass, plastic, polymeric or other non-magnetically active insert may be placed inside the second post to impart rigidity. In some examples, the first post and/or the second post may comprise a magnetic material, such as an earth magnet, embedded within the material comprising the post. For example, a 1 $mm^3$ neodymium magnet may be embedded within the tip of the first post. The posts may comprise a polymer, such as PDMS polymer.

The process in FIG. 6 may continue from action 610 to action 620, "Detect, by a magnetometer situated proximate to the first post, a change in a magnetic field resulting from a deflection of the first post in a first direction from a first position to a second position." At action 620, a magnetometer (such as magnetometer 120 depicted in FIG. 1) may be situated proximate to the first, flexible post. The magnetometer may be effective to detect a change in a magnetic field resulting from deflection of the first post as the first post may include a magnetic material, as described herein. In various examples, the first post may be flexible and may be deflected by contraction of the cardiac tissue adhered to the first post and disposed between the first post and the second post.

The process in FIG. 6 may continue from action 620 to action 630, "Generate a signal corresponding to the change in the magnetic field." At action 630, a signal may be generated by the magnetometer in response to the changing magnetic field. For example, in cases where the magnetometer is a GMR sensor, a voltage of the signal generated by the GMR sensor may be modulated by the changes in the magnetic field detected by the GMR sensor. The changes in the magnetic field detected by the GMR sensor may result from movement of the magnet embedded within the flexible first post due to the contraction of the cardiac tissue adhered to the first and second posts.

The process in FIG. 6 may continue from action 630 to action 640, "Filter the signal by filtering out frequencies of the signal outside of a first frequency range to produce a filtered signal, wherein the first frequency range includes frequencies associated with beating of cardiac tissue." At action 640 the signal generated by the magnetometer (e.g., a GMR sensor or other magnetic sensor) may be filtered by filtering out frequencies of the signal outside of a first frequency range. The first frequency range may be a frequency or a range of frequencies associated with the beating of the cardiac tissue adhered to the first and second post. Accordingly, magnetic field noise resulting from temperature fluctuation and/or ambient magnetic fields in the local environment may be filtered out and the magnetic field change resulting from the beating of the cardiac tissue may be detected. The cutoff frequencies of the filter used may reflect the expected range of frequencies of the cardiac tissue under observation. Additionally, in some examples, the filters may be designed in order to filter out noise resulting from the particular environment. For example, various frequencies of unwanted noise may be produced in the local environment due to machinery and/or other ambient conditions. The particular filters used may be designed to maximize the signal to noise ratio for the particular environment and conditions.

The process in FIG. 6 may continue from action 640 to action 650, "Determine a force exerted by the cardiac tissue based at least in part on the filtered signal." At action 650, a force exerted by the cardiac tissue may be determined based at least in part on the signal output by the magnetometer and filtered by the electronic frequency filters. Calculations used to determine the force exerted by the cardiac tissue may be performed by a data acquisition device as described above in FIG. 1. Additionally, data generated by the magnetometers and calculated by the data acquisition device may be stored in a memory. Accordingly, the embodiments described herein may allow for real-time and massively parallel monitoring of cardiac tissue with minimal data storage and processing requirements relative to optical techniques for monitoring cardiac tissue.

Figure 7:
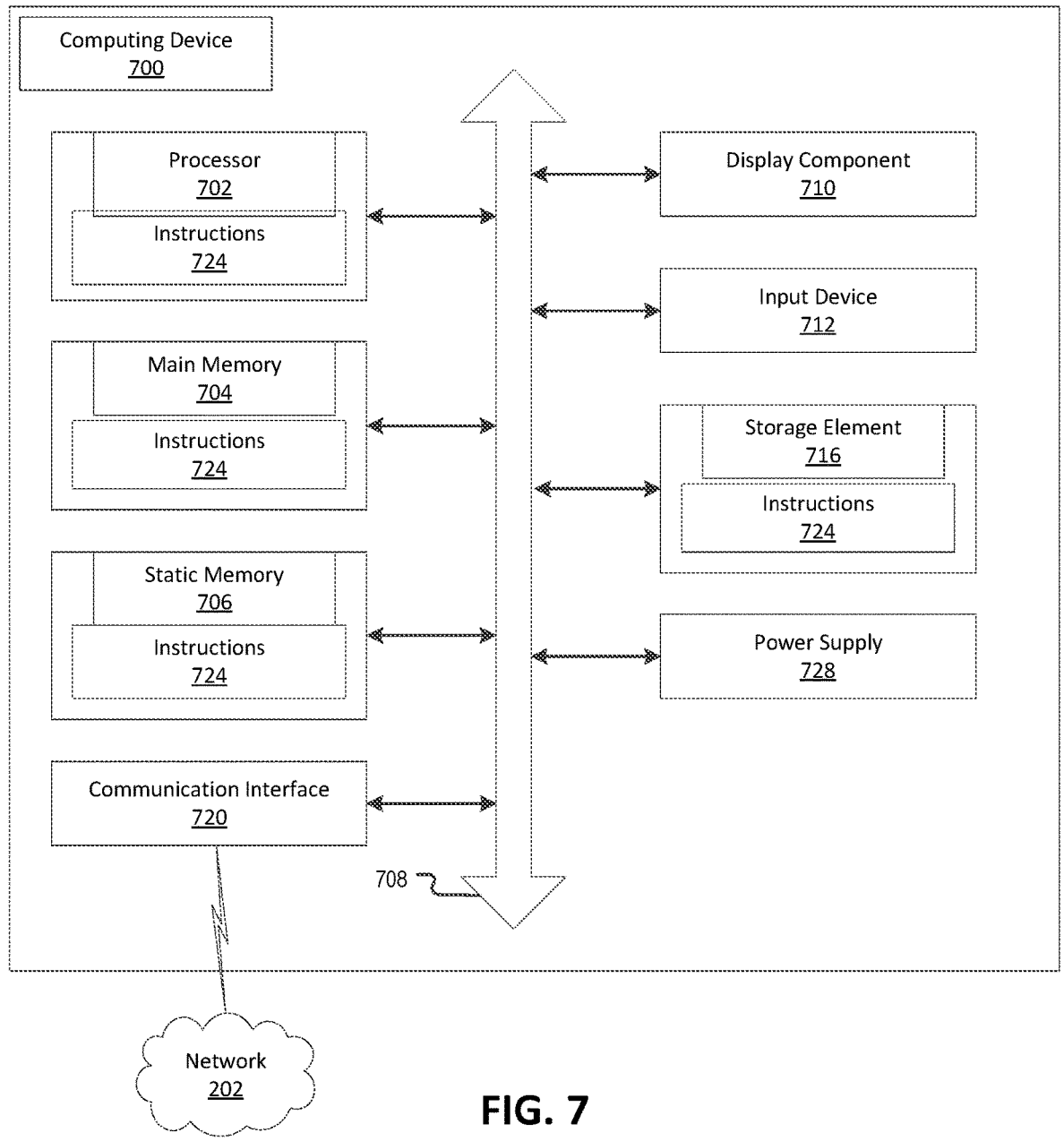
FIG. 7 depicts an example computing device effective to perform the various processing techniques described herein.

Referring to FIG. 7, the block diagram illustrates components of a computing device 700, according to some example embodiments, able to read instructions 724 from a non-transitory machine-readable storage medium (e.g., a hard drive storage system) and perform any one or more of the methodologies discussed herein, in whole or in part. Specifically, FIG. 7 shows the computing device 700 in the example form of a computer system within which the instructions 724 (e.g., software, a program, an application, an applet, an app, or other executable code) for causing the computing device 700 to perform any one or more of the methodologies discussed herein may be executed, in whole or in part. For example, the computing device 700 may be effective to execute all or a part of the method described above in reference to FIG. 6. Additionally, in some examples, the computing device may perform the functions of the data acquisition system described above with respect to FIG. 1.

In alternative embodiments, the computing device 700 operates as a standalone device or may be connected (e.g., networked) to other computing devices. In a networked deployment, the computing device 700 may operate in the capacity of a server computing device or a client computing device in a server-client network environment, or as a peer computing device in a distributed (e.g., peer-to-peer) network environment. The computing device 700 may include hardware, software, or combinations thereof, and may, as for example, be a server computer, a client computer, a personal computer (PC), a tablet computer, a laptop computer, a netbook, a cellular telephone, a smartphone, a set-top box (STB), a personal digital assistant (PDA), a web appliance, a network router, a network switch, a network bridge, or any computing device capable of executing the instructions 724, sequentially or otherwise, that specify actions to be taken by that computing device. Further, while only a single computing device 700 is illustrated, the term "computing device" shall also be taken to include any collection of computing devices that individually or jointly execute the instructions 724 to perform all or part of any one or more of the methodologies discussed herein.

The computing device 700 includes a processor 702 (e.g., a central processing unit (CPU), a graphics processing unit (GPU), a digital signal processor (DSP), an application specific integrated circuit (ASIC), a radio-frequency integrated circuit (RFIC), or any suitable combination thereof), a main memory 704, and a static memory 706, which are configured to communicate with each other via a bus 708. The processor 702 may contain microcircuits that are configurable, temporarily or permanently, by some or all of the instructions 724 such that the processor 702 is configurable to perform any one or more of the methodologies described herein, in whole or in part. For example, a set of one or more microcircuits of the processor 702 may be configurable to execute one or more modules (e.g., software modules) described herein.

The computing device 700 may further include a display component 710. The display component 710 may comprise, for example, one or more devices such as cathode ray tubes (CRTs), liquid crystal display (LCD) screens, gas plasma-based flat panel displays, LCD projectors, or other types of display devices.

The computing device 700 may include one or more input devices 712 operable to receive inputs from a user. The input devices 712 can include, for example, a push button, touch pad, touch screen, wheel, joystick, keyboard, mouse, trackball, keypad, accelerometer, light gun, game controller, or any other such device or element whereby a user can provide inputs to the computing device 700. These input devices 712 may be physically incorporated into the computing device 700 or operably coupled to the computing device 700 via wired or wireless interface. For computing devices with touchscreen displays, the input devices 712 can include a touch sensor that operates in conjunction with the display component 710 to permit users to interact with the image displayed by the display component 706 using touch inputs (e.g., with a finger or stylus). In some examples, the magnetometer 120 and/or filter 130 described above with respect to FIG. 1 may be examples of input devices 712 operable to provide inputs to computing device 700.

The computing device 700 may also include at least one communication interface 720, comprising one or more wireless components operable to communicate with one or more separate devices within a communication range of the particular wireless protocol. The wireless protocol can be any appropriate protocol used to enable devices to communicate wirelessly, such as Bluetooth, cellular, IEEE 802.11, or infrared communications protocols, such as an IrDA-compliant protocol. It should be understood that the communication interface 720 may also or alternatively comprise one or more wired communications interfaces for coupling and communicating with other devices.

The computing device 700 may also include a power supply 728, such as, for example, a rechargeable battery operable to be recharged through conventional plug-in approaches or through other approaches, such as capacitive charging. Alternatively, the power supply 728 may comprise a power supply unit which converts AC power from the power grid to regulated DC power for the internal components of the device 700.

The computing device 700 may also include a storage element 716. The storage element 716 includes the machine-readable medium on which are stored the instructions 724 embodying any one or more of the methodologies or functions described herein. The instructions 724 may also reside, completely or at least partially, within the main memory 704, within the processor 702 (e.g., within the processor's cache memory), or both, before or during execution thereof by the computing device 700. The instructions 724 may also reside in the static memory 706.

Accordingly, the main memory 704 and the processor 702 may also be considered machine-readable media (e.g., tangible and non-transitory machine-readable media). The instructions 724 may be transmitted or received over a network 202 via the communication interface 720. For example, the communication interface 720 may communicate the instructions 724 using any one or more transfer protocols (e.g., HTTP).

The computing device 700 may be implemented as any of a number of electronic devices, such as a tablet computing device, a smartphone, a media player, a portable gaming device, a portable digital assistant, a laptop computer, or a desktop computer. In some example embodiments, the computing device 700 may have one or more additional input components (e.g., sensors or gauges) (not shown). Examples of such input components include an image input component (e.g., one or more cameras), an audio input component (e.g., a microphone), a direction input component (e.g., a compass), a location input component (e.g., a GPS receiver), an orientation component (e.g., a gyroscope), a motion detection component (e.g., one or more accelerometers), an altitude detection component (e.g., an altimeter), and a gas detection component (e.g., a gas sensor). Inputs harvested by any one or more of these input components may be accessible and available for use by any of the modules described herein.

As used herein, the term "memory" refers to a non-transitory machine-readable medium capable of storing data temporarily or permanently and may be taken to include, but not be limited to, random-access memory (RAM), read-only memory (ROM), buffer memory, flash memory, and cache memory. The machine-readable medium is non-transitory in that it does not embody a propagating signal. While the machine-readable medium is described in example embodiments as a single medium, the term "machine-readable medium" should be taken to include a single medium or multiple media (e.g., a centralized or distributed database, or associated caches and servers) able to store instructions 724. The term "machine-readable medium" shall also be taken to include any medium, or combination of multiple media, that is capable of storing the instructions 724 for execution by the computing device 700, such that the instructions 724, when executed by one or more processors of the computing device 700 (e.g., processor 702), cause the computing device 700 to perform any one or more of the methodologies described herein, in whole or in part. Accordingly, a "machine-readable medium" refers to a single storage apparatus or device as well as cloud-based storage systems or storage networks that include multiple storage apparatus or devices. The term "machine-readable medium" shall accordingly be taken to include, but not be limited to, one or more tangible (e.g., non-transitory) data repositories in the form of a solid-state memory, an optical medium, a magnetic medium, or any suitable combination thereof.

While the invention has been described in terms of particular embodiments and illustrative figures, those of ordinary skill in the art will recognize that the invention is not limited to the embodiments or figures described. For example, in various embodiments described above, a single pair of polymeric posts are described between which heart tissue is cultured. However, in other embodiments, an array of post-pairs may be arranged on one or more common bases, with each post-pair having cardiac tissue cultured between, and affixed to, the post-pairs.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show details of the invention in more detail than is necessary for the fundamental understanding of the invention, the description taken with the drawings and/or examples making apparent to those skilled in the art how the several forms of the invention may be embodied in practice.

Embodiments of the disclosure can be described in view of the following clauses:

1. A cardiac tissue analysis device comprising:
a base;
a first post having a proximal end coupled to the base and a distal end, wherein the first post comprises a magnetic portion;
a second post having a proximal end coupled to the base and a distal end, wherein the distal end of the second post is separated from the distal end of the first post by a gap;
a magnetometer disposed proximate to the first post for detecting deflection of the distal end of the first post by generating a signal in response to movement of the magnetic portion of the first post; and
a filter circuit communicatively coupled to the magnetometer, the filter circuit effective to pass signals of a first frequency range, wherein the first frequency range includes frequencies associated with beating of cardiac tissue.

2. The cardiac tissue analysis device of Clause 1, wherein the magnetometer comprises a giant magnetoresistive (GMR) sensor.

3. The cardiac tissue analysis device of Clause 2, wherein the GMR sensor comprises a plurality of resistances arranged in a Wheatstone bridge configuration, and wherein the GMR sensor is effective to decrease a voltage of the signal due to an increase in magnetic field detected by the GMR sensor.

4. The cardiac tissue analysis device of any of Clauses 1-3, further comprising an electromagnetic coil adjacent to the first post such that when a first current is supplied to the electromagnetic coil, the electromagnetic coil is effective to displace the distal end of the first post by attracting the magnetic portion of the first post.

5. The cardiac tissue analysis device of any of Clauses 1-3, further comprising a permanent magnet adjacent to the first post effective to attract the magnetic portion of the first post with a first force.

6. The cardiac tissue analysis device of any of Clauses 1-5, wherein the filter comprises a high-pass filter with a cutoff frequency of between 0.01 Hz and 0.3 Hz.

7. The cardiac tissue analysis device of any of Clauses 1-6, wherein the first post and the second post comprise polydimethylsiloxane.

8. The cardiac tissue analysis device of any of Clauses 1-7, wherein the second post comprises a rigid insert effective to prevent movement of the second post in response to contraction of cardiac tissue coupled to the first post and the second post.

9. The cardiac tissue analysis device of Clause 1, further comprising an electromagnetic coil adjacent to the first post, wherein the electromagnetic coil is effective to:

attract the magnetic portion of the first post with a first force when a first current is supplied to the electromagnetic coil; and attract the magnetic portion of the first post with a second force when a second current is supplied to the electromagnetic coil, wherein the second current is greater than the first current.

10. A method comprising:

culturing cardiac tissue adhered to a first post and a second post, wherein the first post comprises a magnetic portion;

detecting a change in a magnetic field resulting from a deflection of the first post in a first direction from a first position to a second position;

generating a signal corresponding to the change in the magnetic field;

filtering the signal by filtering out frequencies of the signal outside of a first frequency range to produce a filtered signal, wherein the first frequency range includes frequencies associated with beating of cardiac tissue; and determining a force exerted by the cardiac tissue based at least in part on the filtered signal.

11. The method of Clause 10, wherein the detecting the change in the magnetic field comprises detecting with a magnetometer situated proximate to the first post the change in the magnetic field.

12. The method of any of Clauses 10-11, wherein the change in the magnetic field resulting from the deflection of the first post from the first position to the second position results from a contraction of the cardiac tissue.

13. The method of any of Clauses 10-12, further comprising attracting the magnetic portion of the first post with an external magnet such that the first post is deflected in a second direction opposite the first direction.

14. The method of any of Clauses 10-13, further comprising applying a first current to an external electromagnetic coil at a first time during a cardiac cycle of the cardiac tissue to stress the cardiac tissue by a first amount.

15. The method of Clause 14, further comprising applying a second current to the external electromagnetic coil at a second time during the cardiac cycle of the cardiac tissue to stress the cardiac tissue by a second amount different from the first amount.

16. The method of any of Clauses 10-15, further comprising:

subjecting the cardiac tissue to a therapeutic agent for a period of time;

detecting, by the magnetometer situated proximate to the first post, a second change in a magnetic field resulting from a second deflection of the first post from the first position to a third position;

generating a second signal corresponding to the second change in the magnetic field;

filtering the second signal by filtering out frequencies of the second signal outside of the first frequency range to produce a second filtered signal; and determining a second force exerted by the cardiac tissue based at least in part on the second filtered signal.

17. A method comprising:

culturing cardiac tissue such that the cardiac tissue adheres to a first post and a second post, wherein the first post comprises a magnetic portion;

exposing the cardiac tissue to a therapeutic agent;

generating a signal in response to changes in a magnetic field caused by movement of the magnetic portion of the first post resulting from deflection of the first post due to contraction of the cardiac tissue;

filtering the signal by filtering out frequencies of the signal outside of a first frequency range to produce a filtered signal, wherein the first frequency range includes frequencies associated with beating of cardiac tissue; and determining, based at least in part on the filtered signal, changes in force exerted by the cardiac tissue over time.

18. The method of Clause 17, further comprising:

positioning the first post and the second post in a well of a multi-well plate; and adding the therapeutic agent to the well.

19. The method of any of Clauses 17-18, wherein the generating the signal in response to changes in the magnetic field comprises detecting movement of the magnetic portion of the first with a magnetometer positioned proximate to the first post.

20. The method of any of Clauses 17-19, further comprising inducing movement of the first post by applying a magnetic field to the magnetic portion of the first post.

21. The method of Clause 20, wherein the applying the magnetic field to the magnetic portion of the first post comprises applying a first current to an external electromagnetic coil to induce a first strain in the cardiac tissue.

22. The method of Clause 21, wherein the applying the magnetic field to the magnetic portion of the first post comprises applying a second current to the external electromagnetic coil to induce a second strain in the cardiac tissue, wherein the second strain is different than the first strain.

As used herein and unless otherwise indicated, the terms "a" and "an" are taken to mean "one," "at least one" or "one or more." Unless otherwise required by context, singular terms used herein shall include pluralities and plural terms shall include the singular.

Unless the context clearly requires otherwise, throughout the description and the claims, the words "comprise," "comprising," and the like are to be construed in an inclusive sense as opposed to an exclusive or exhaustive sense; that is to say, in the sense of "including, but not limited to." Words using the singular or plural number also include the plural and singular number, respectively. Additionally, the words "herein," "above," and "below" and words of similar import, when used in this application, shall refer to this application as a whole and not to any particular portions of the application.

The description of embodiments of the disclosure is not intended to be exhaustive or to limit the disclosure to the precise form disclosed. While specific embodiments and examples for the disclosure are described herein for illustrative purposes, various equivalent modifications are possible within the scope of the disclosure, as those skilled in the relevant art will recognize. Such modifications may include, but are not limited to, changes in the dimensions and/or the materials shown in the disclosed embodiments.

Specific elements of any embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

Therefore, it should be understood that the invention can be practiced with modification and alteration within the spirit and scope of the appended claims. The description is not intended to be exhaustive or to limit the invention to the precise form disclosed. It should be understood that the invention can be practiced with modification and alteration and that the invention be limited only by the claims and the equivalents thereof.

What is claimed is:

1. A tissue analysis device, comprising:
   a base;
   a first post having a proximal end coupled to the base and a distal end, wherein the first post comprises a magnetic portion, the first post being configured to have a tissue attached thereto;
   a second post having a proximal end coupled to the base and a distal end, wherein the distal end of the second post is separated from the distal end of the first post by a gap, wherein the second post is configured to have the tissue attached thereto such that the tissue extends across the gap;
   a magnetometer disposed proximate to the first post such that the magnetometer is configured to detect a deflection of the magnetic portion of the first post and to generate a signal in response to the deflection of the magnetic portion of the first post; and
   a non-transitory machine readable storage medium storing instructions, which when executed by a processor, causes the processor to perform operations, including:
      determining a force exerted by the tissue based upon a known force corresponding to the signal.

2. The tissue analysis device of claim 1, wherein the magnetometer comprises a giant magnetoresistive (GMR) sensor.

3. The tissue analysis device of claim 1, wherein the first post and the second post are disposed in a well of a multi-well plate.

4. The tissue analysis device of claim 1, further comprising an electromagnetic coil adjacent to the first post such that when a first current is supplied to the electromagnetic coil, the electromagnetic coil is configured to displace the distal end of the first post by attracting the magnetic portion of the first post.

5. The tissue analysis device of claim 1, further comprising a permanent magnet adjacent to the first post configured to attract the magnetic portion of the first post with a first force.

6. The cardiac tissue analysis device of claim 1, further comprising a filter circuit communicatively coupled to the magnetometer and configured to pass signals of a first frequency range to the processor, wherein the first frequency range includes frequencies associated with the tissue.

7. The tissue analysis device of claim 1, wherein the first post and the second post comprise polydimethylsiloxane.

8. The tissue analysis device of claim 1, wherein the second post comprises a rigid insert configured to prevent movement of the second post in response to contraction of the tissue coupled to the first post and the second post.

9. The tissue analysis device of claim 1, further comprising an electromagnetic coil adjacent to the first post, wherein the electromagnetic coil is configured to:

attract the magnetic portion of the first post with a first force when a first current is supplied to the electromagnetic coil; and
attract the magnetic portion of the first post with a second force when a second current is supplied to the electromagnetic coil, wherein the second current is greater than the first current.

10. A method, comprising:
   culturing a tissue adhered to a first post and a second post of a tissue analysis device, wherein the first post comprises a magnetic portion;
   detecting a change in a magnetic field resulting from a deflection of the first post in a first direction from a first position to a second position;
   generating a signal corresponding to the change in the magnetic field; and
   determining a force exerted by the tissue based at least in part on the signal.

11. The method of claim 10, wherein detecting the change in the magnetic field comprises detecting with a magnetometer situated proximate to the first post the change in the magnetic field.

12. The method of claim 10, wherein the change in the magnetic field resulting from the deflection of the first post from the first position to the second position results from a contraction of the tissue.

13. The method of claim 10, further comprising attracting the magnetic portion of the first post with an external magnet such that the first post is deflected in a second direction opposite the first direction.

14. The method of claim 10, further comprising applying a first current to an external electromagnetic coil at a first time during a cycle of the tissue to stress the tissue by a first amount.

15. The method of claim 10, further comprising producing a filtered signal prior to determining the force of the tissue by filtering out a second frequency range of the signal outside of a first frequency range, the first frequency range including frequencies associated with the tissue, wherein determining the force is based on the filtered signal.

16. The method of claim 15, further comprising:
   subjecting the tissue to a therapeutic agent for a period of time;
   detecting, by the magnetometer situated proximate to the first post, a second change in a magnetic field resulting from a second deflection of the first post from the first position to a third position;
   generating a second signal corresponding to the second change in the magnetic field;
   filtering out frequencies of the second signal outside of the first frequency range to produce a second filtered signal; and
   determining a second force exerted by the tissue based at least in part on the second filtered signal.

17. A method comprising:
   culturing a tissue such that the tissue adheres to a first post and a second post of a tissue analysis device, wherein the first post comprises a magnetic portion;
   exposing the tissue to a therapeutic agent;
   generating a signal in response to a change in a magnetic field caused by movement of the magnetic portion of the first post resulting from deflection of the first post due to contraction of the tissue;
   filtering out frequencies of the signal outside of a first frequency range to produce a filtered signal, wherein the first frequency range includes frequencies associated with the tissue; and determining, based at least in part on the filtered signal, changes in force exerted by the tissue over time.

18. The method of claim 17, further comprising: positioning the first post and the second post in a well of a multi-well plate; and adding the therapeutic agent to the well.

19. The method of claim 17, wherein the generating the signal in response to changes in the magnetic field comprises detecting movement of the magnetic portion of the first with a magnetometer positioned proximate to the first post.

20. The method of claim 17, further comprising inducing movement of the first post by applying a magnetic field to the magnetic portion of the first post.

21. The method of claim 20, wherein the applying the magnetic field to the magnetic portion of the first post comprises applying a first current to an external electromagnetic coil to induce a first strain in the tissue.

22. The method of claim 21, wherein the applying the magnetic field to the magnetic portion of the first post comprises applying a second current to the external electromagnetic coil to induce a second strain in the tissue, wherein the second strain is different than the first strain.

* * * * *

UNITED STATES PATENT AND TRADEMARK OFFICE
CERTIFICATE OF CORRECTION

PATENT NO. : 11,331,027 B2  
APPLICATION NO. : 16/082847  
DATED : May 17, 2022  
INVENTOR(S) : N. Sniadecki et al.

Page 1 of 1

It is certified that error appears in the above-identified patent and that said Letters Patent is hereby corrected as shown below:

In the Claims

| Column | Line | |
| --- | --- | --- |
| 19 | 54 | Claim 6 Line 1, change "cardiac tissue" to -- tissue -- |

Signed and Sealed this  
Thirteenth Day of June, 2023

Katherine Kelly Vidal  
*Director of the United States Patent and Trademark Office*